(12) United States Patent
Kataoka et al.

(10) Patent No.: US 7,897,176 B2
(45) Date of Patent: Mar. 1, 2011

(54) COMPOSITION CONTAINING FINE PARTICLES FOR SUPPORTING BIOLOGICALLY ACTIVE SUBSTANCE THEREON OR HAVING THE SAME SUPPORTED THEREON AND METHOD FOR PREPARING THESE

(75) Inventors: Kazunori Kataoka, Tokyo (JP); Yoshinori Kakizawa, Tsukuba (JP)

(73) Assignee: Toudai TLO, Ltd., Tokyo (JP)

( * ) Notice: Subject to any disclaimer, the term of this patent is extended or adjusted under 35 U.S.C. 154(b) by 1198 days.

(21) Appl. No.: 10/487,713

(22) PCT Filed: Aug. 27, 2002

(86) PCT No.: PCT/JP02/08619

§ 371 (c)(1),
(2), (4) Date: Feb. 26, 2004

(87) PCT Pub. No.: WO03/018690

PCT Pub. Date: Mar. 6, 2003

(65) Prior Publication Data

US 2004/0197360 A1 Oct. 7, 2004

(30) Foreign Application Priority Data

Aug. 27, 2001 (JP) ............................. 2001-256125

(51) Int. Cl.
*A61K 9/14* (2006.01)
*A61K 8/02* (2006.01)
*A61K 8/64* (2006.01)

(52) U.S. Cl. ...................... 424/489; 424/401; 424/70.14

(58) Field of Classification Search ................. 424/401, 424/70.14
See application file for complete search history.

(56) References Cited

U.S. PATENT DOCUMENTS

| 5,368,869 | A | * | 11/1994 | Savello et al. .................. 426/42 |
| 6,436,386 | B1 | * | 8/2002 | Roberts et al. ........... 424/78.17 |
| 2003/0017206 | A1 | | 1/2003 | Seo et al. |
| 2003/0059398 | A1 | | 3/2003 | Ranger et al. |

(Continued)

FOREIGN PATENT DOCUMENTS

JP 5-17111 1/1993

(Continued)

OTHER PUBLICATIONS

Helmut ("Double-Hydrophilic Block Copolymers: Synthesis and Application as Novel Surfactants and Crystal Growth Modifiers" in Macromol. Rapid Commun, Mar. 7, 2001, vol. 22, pp. 219-252.*

(Continued)

*Primary Examiner*—Blessing M Fubara
(74) *Attorney, Agent, or Firm*—Wenderoth, Lind & Ponack, L.L.P.

(57) ABSTRACT

Provided are a dispersion comprising organic-inorganic hybrid type particles carried thereon with a biologically active substance, wherein the above particles can be obtained by allowing a block copolymer represented by Formula (I):

PEG-block-poly(carbo)     (I)

(wherein PEG represents a polyethylene glycol segment, and carbo represents a repetitive unit having a carboxylate ion on a side chain) and an aqueous medium system capable of forming hydroxyapatite to coexist with the biologically active substance, and a preparing method for the same.

11 Claims, 10 Drawing Sheets

(a)

(b)

U.S. PATENT DOCUMENTS

2004/0072784 A1     4/2004    Sant et al.
2005/0244501 A1    11/2005   Ranger et al.

FOREIGN PATENT DOCUMENTS

WO      02/100439     12/2002
WO      03/000778      1/2003

OTHER PUBLICATIONS

Kataoka et al. ("Spontaneous Formation of Polyion Complex Micelles with Narrow Distribution from Antisense Oligonucleotide and Cationic Block Copolymer in Physiological Saline," in Macromolecules, 1996, 29, pp. 8556-8557).*

Yasunori Kakizawa et al., "Block Kyojugotai to DNA kara narau Jiko Soshikika Ryushi no Sosei to sono Saibonai DNA Donyu System eno Tenkai", Polymer Preprints, Japan, vol. 50, No. 14, pp. 3818-3819, Aug. 28, 2001.

Helmut Cölfen, "Double-Hydrophilic Block Copolymers: Synthesis and Application as Novel Surfactants and Crystal Growth Modifiers", Macromol. Rapid Commun., vol. 22, pp. 219-252, 2001.

* cited by examiner (a)

(b)

Confocal microscopic image

A   Fluorescent image        Bright field image

DNA only

B

CaP precipitate (PEG-PAA 70ug/mL)

C  Fluorescent image     Bright field image

CaP particle (PEG-PAA 280ug/ml)
In the non-coexistence of poly(methacrylic acid)

D

CaP particle (PEG-PAA 280ug/ml)
In the coexistence of poly(methacrylic acid)
arrow: nucleus

A

B

COMPOSITION CONTAINING FINE PARTICLES FOR SUPPORTING BIOLOGICALLY ACTIVE SUBSTANCE THEREON OR HAVING THE SAME SUPPORTED THEREON AND METHOD FOR PREPARING THESE

TECHNICAL FIELD

The present invention relates to a composition containing organic-inorganic hybrid particles for carrying a biologically active substance or carried thereon with it and a method for preparing them. The above biologically active substance can preferably be a high molecular polyvalent anionically chargeable compound (for example, poly- or oligonucleotide and poly- or oligopeptide).

BACKGROUND ART

A crystal of calcium phosphate (hydroxyapatite) formed when a calcium aqueous solution is mixed with a phosphoric acid aqueous solution so that a supersaturation state is obtained has a property to bond with DNA. A method in which calcium phosphate and DNA are coprecipitated making use of this property has been widely utilized as a method for introducing DNA into a cell. The problems of this method include a very narrow range of an optimum condition, which makes handling thereof difficult, and less liability to obtain reproducibility. In particular, growth in the crystal of calcium phosphate is very fast to form the giant crystal, and therefore it is pointed out that an efficiency of introducing DNA is reduced if a calcium aqueous solution and a phosphoric acid aqueous solution are not quickly worked on a cell after mixing. Also, hydroxyapatite is used as a base substance (for example, a carrier for chromatography) for adsorbing a biologically active substance including polynucleotide such as DNA, other peptides or polypeptide.

In the foregoing method for introducing DNA (or gene) into a cell, development of a method for controlling a growth in a crystal of calcium phosphate and a particle diameter thereof is considered to be important to a rise in an introducing efficiency of DNA, a reproducibility and a storage stability. Further, if substances carried or adsorbed on such crystal can widely be used as various biologically active substances without being restricted to DNA described above and a particle diameter of a particle formed can be controlled, it is considered to be important in providing a carrier system which can widely be used for carrying medicines or a delivery system for medicines. Accordingly, an object of the present invention is to provide a composition useful for forming particles which not only enhance an efficiency of introducing DNA into a cell but also have a wide and controlled particle diameter and which can stably carry a biologically active substance and conveniently deliver the biologically active substance to a target cell, a desired tissue or a local site.

DISCLOSURE OF THE INVENTION

The present inventors have continued researches in order to control a growth in a crystal of calcium phosphate (mainly hydroxyapatite) in an aqueous solution containing a calcium ion and a phosphoric acid ion and a particle diameter thereof. As a result thereof, they have found that calcium phosphate particles into which DNA or the other biologically active substances is introduced or in which they coexist can be formed while controlling a particle diameter thereof when a calcium ion is reacted with a phosphoric acid ion under the coexistence of DNA or the other biologically active substances in an aqueous solution in which present is a specific block copolymer containing a hydrophilic and nonionic polyethylene glycol (PEG) segment and a polyanionic segment originating in a carboxyl group. In addition thereto, it has been confirmed that a particle diameter of such particles can be controlled, if necessary, to a submicron order (several 100 nm) or less and that an aqueous dispersion system containing such particles can stably be stored under an ambient condition without producing precipitates. Further, it has been found as well that such aqueous dispersion system can be turned into a composition of a dried type (for example, freeze-dried) and that it can be then reconstituted to the same aqueous dispersion system.

Hence, according to the present invention, provided is an aqueous composition for forming (or used for forming) organic-inorganic hybrid type particles carried thereon with a biologically active substance, wherein the particles described above comprise a block copolymer having a structure represented by Formula (I):

PEG-block-poly(carbo)    (I)

(wherein PEG represents a polyethylene glycol segment, and carbo represents a repetitive unit having a carboxylate ion on a side chain), a calcium ion ($Ca^{+2}$) and a phosphoric acid ion ($PO_4^{3-}$) as essential components.

Further, provided as another embodiment of the present invention is a composition comprising organic-inorganic hybrid type particles carried thereon with a biologically active substance, wherein the particles described above are formed from a block copolymer having a structure represented by Formula (I):

PEG-block-poly(carbo)    (I)

(wherein PEG represents a polyethylene glycol segment, and carbo represents a repetitive unit having a carboxylate ion at a side chain), a calcium ion ($Ca^{+2}$), a phosphoric acid ion ($PO_4^{3-}$) and the above biologically active substance, and the above particles have an average particle diameter of 50 to 60 nm.

Further, provided are an aqueous dispersion composition for forming organic-inorganic hybrid type particles carried thereon with such biologically active substance, a method for preparing a composition containing the above particles carried thereon with a biologically active substance and a method for introducing the above biologically active substance, particularly poly- or oligonucleotide into a cell, comprising a step of incubating the above composition under the coexistence of a cultured cell or injecting it into a suitable part of an animal.

It has so far been known that when a phosphoric acid ion is added to a coagulating solution of modified PEO-block-PMAA (PEO is a polyethylene oxide or polyethylene glycol segment; PMAA is a polymethacrylic acid segment; and among PMAA, three segments are modified with $C_{12}$-alkane) after adding $CaCl_2$, a hybrid type structure of hydroxyapatite/PEG-block-PMAA-$C_{12}$ having a neuronal structure is obtained (*Helmut Cölfen*, Macromol. Rapid Commun. 2001, 22, 219 to 252).

According to the present invention, provided are particles which are substantially spherical regardless of that a biologically active substance is further carried or absent and a means capable of forming uniform particles which have a particle diameter suited for being efficiently introduced into a cell by endocytosis and in which a particle diameter has a narrow distribution. Particles in which a biologically active substance is absent shall be useful as a hydroxyapatite material of a new form comprising fine particles. Further, a system containing particles carried thereon with a biologically active substance shall deliver the biologically active substance to a target and expand a range of a usefulness in the above substance.

B) is a microscopic image in place of a drawing showing the state of a cell after working a precipitate (PEG-PAA 70 μg/ml) of CaP on the cell. In this case, an image showing that the precipitate is adsorbed on the surface of the cell is obtained.

Figure 7:
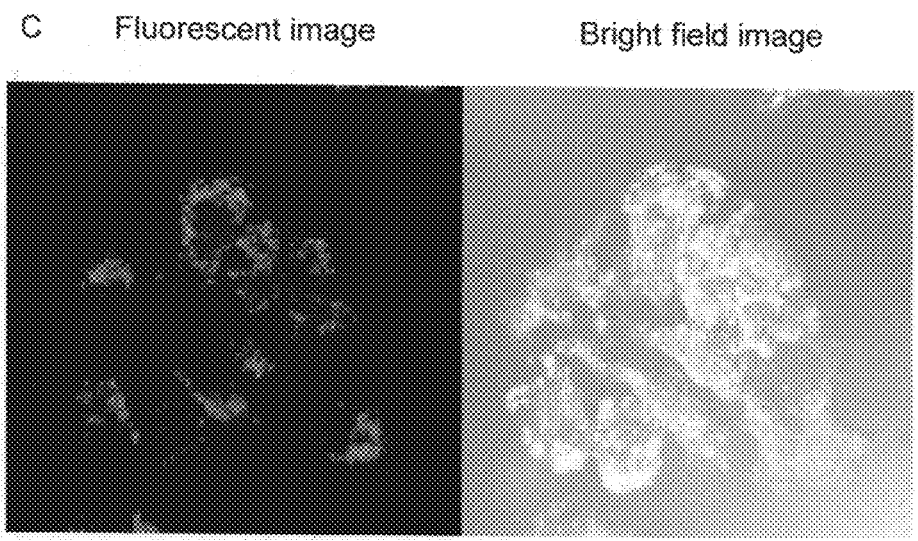
Figure 7:
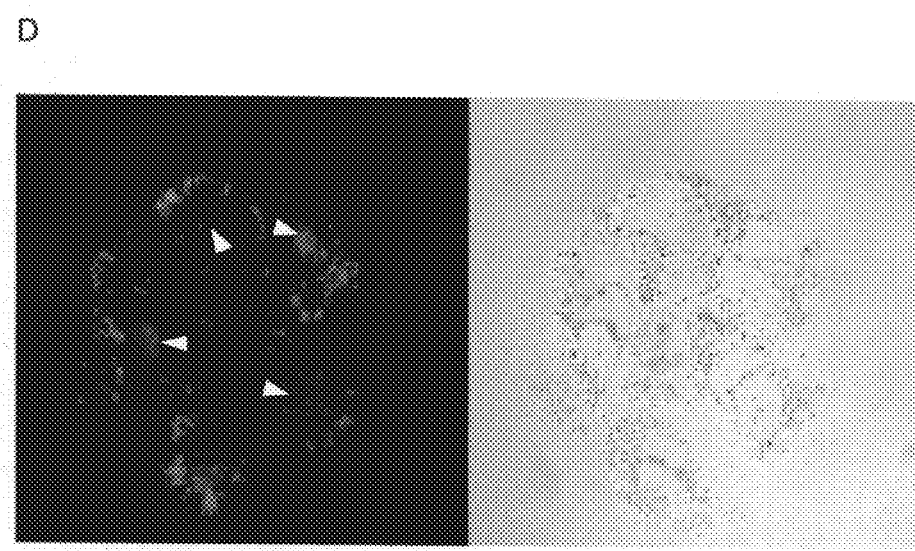

In FIG. 7, C) is a microscopic image in place of a drawing showing the state of a cell after working CaP particles (PEG-PAA 280 μg/ml) (in the non-coexistence of PMA) on the cell. In this case, granular fluorescence indicating introduction of the CaP particles by endocytosis is observed. The same result was obtained in a PEG-PAA of 140 μg/ml.

D) is a microscopic image in place of a drawing showing the state of a cell after working CaP particles (PEG-PAA 280 μg/ml) (in the coexistence of PMA) on the cell. In this case, observed is a fluorescent image showing localization of the CaP particles in a nucleus as well as granular fluorescence indicating that the CaP particles are introduced by endocytosis.

Figure 8:
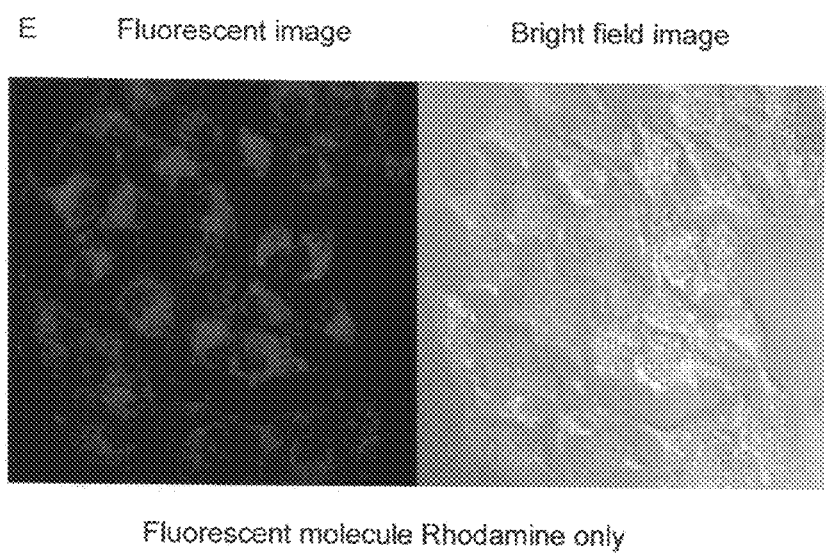

In FIG. 8, E) is a microscopic image in place of a drawing showing the state of a cell after working only a fluorescent molecule Rhodamine on the cell. In this case, fluorescence is observed all over a cytoplasma, and it is shown that a fluorescent molecule does not selectively move to a nucleus.

Figure 9:
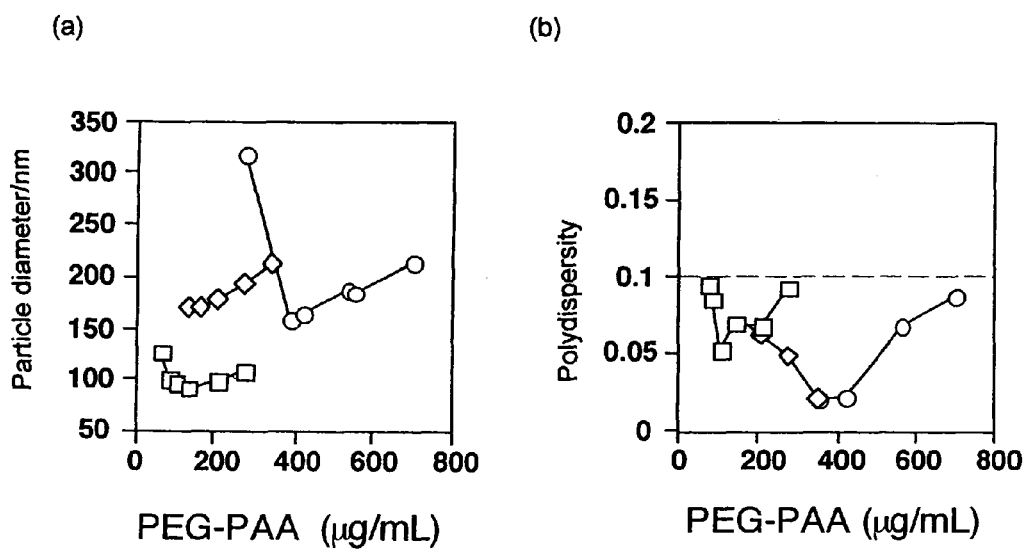

FIG. 9($a$) is a graph showing that a particle diameter of the organic-inorganic hybrid particles according to the present invention changes by a change in a copolymer concentration and a phosphoric acid concentration in Example 9, and ($b$) is a graph showing a polydispersity of the respective particles.

Figure 10:
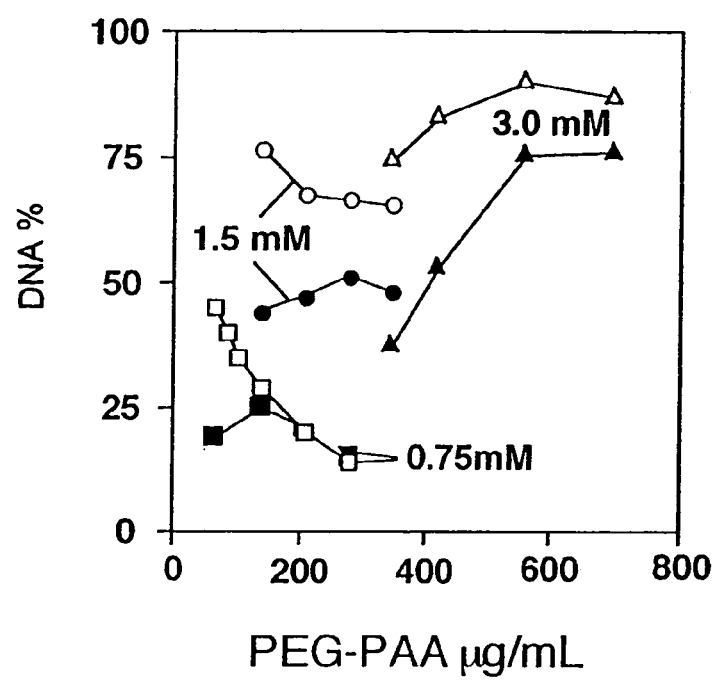

FIG. 10 is a graph showing a dependency of a DNA incorporated amount in the particles on copolymer and phosphoric acid concentrations.

Figure 11:
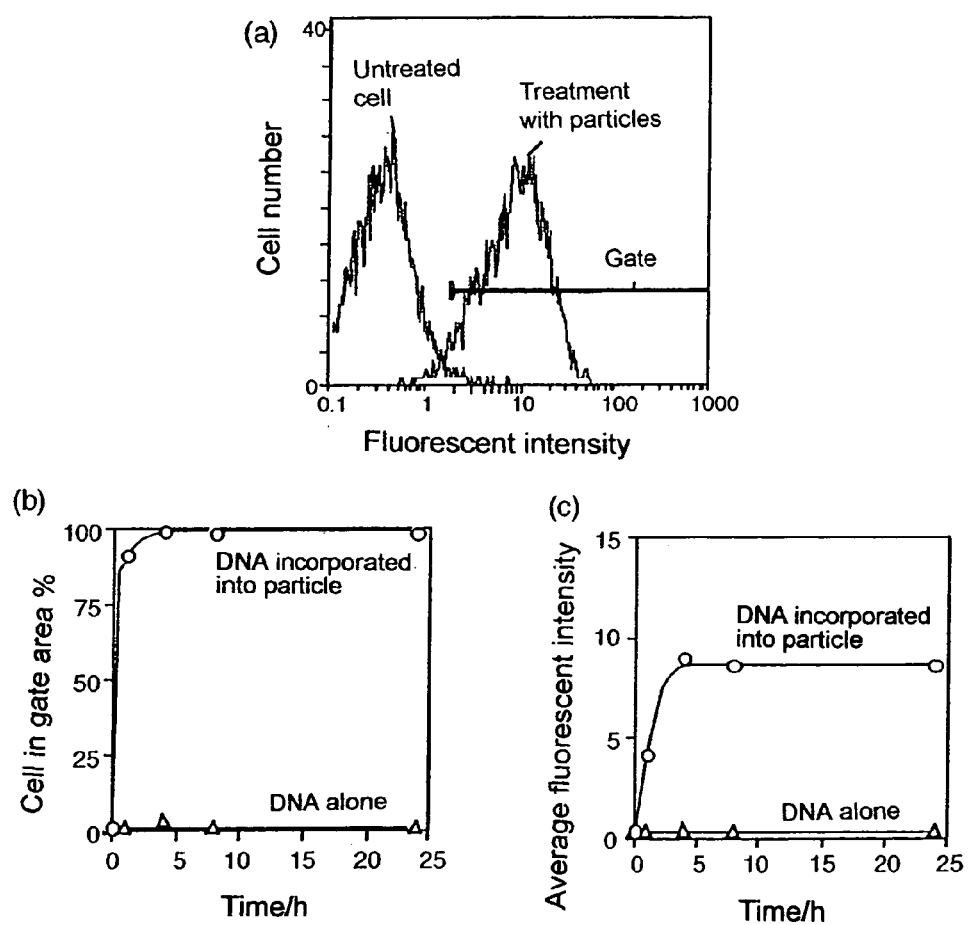

FIG. 11($a$), ($b$) and ($c$) are graphs showing results obtained by evaluating introduction of DNA into a cell in Example 8.

Figure 12:
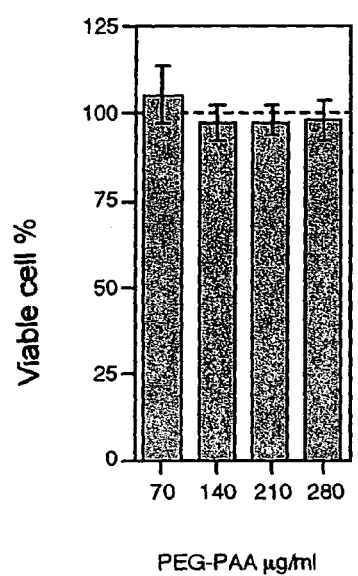

FIG. 12 is a graph showing a result of a test carried out in order to evaluate a toxicity of the particles prepared in Example 9.

Figure 13:
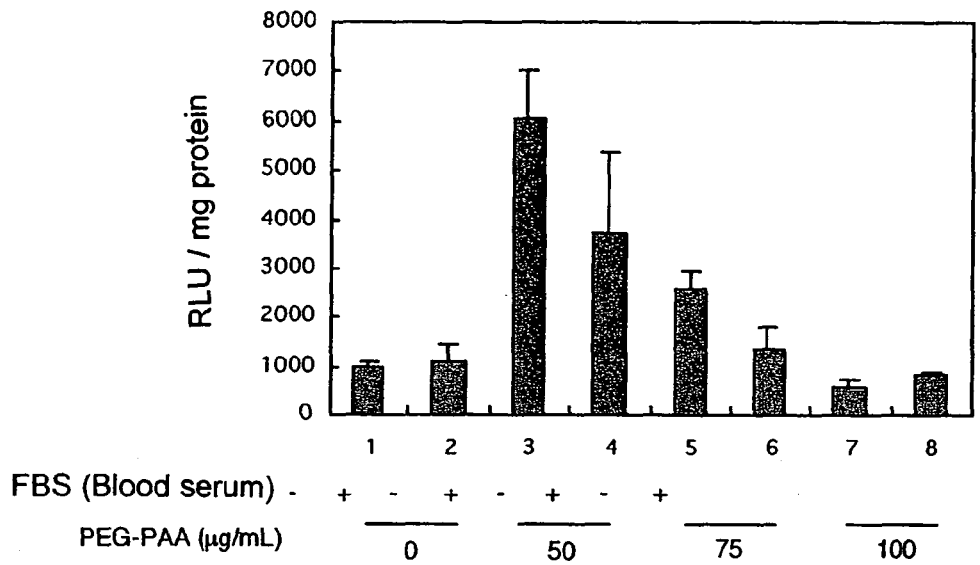
Figure 13:
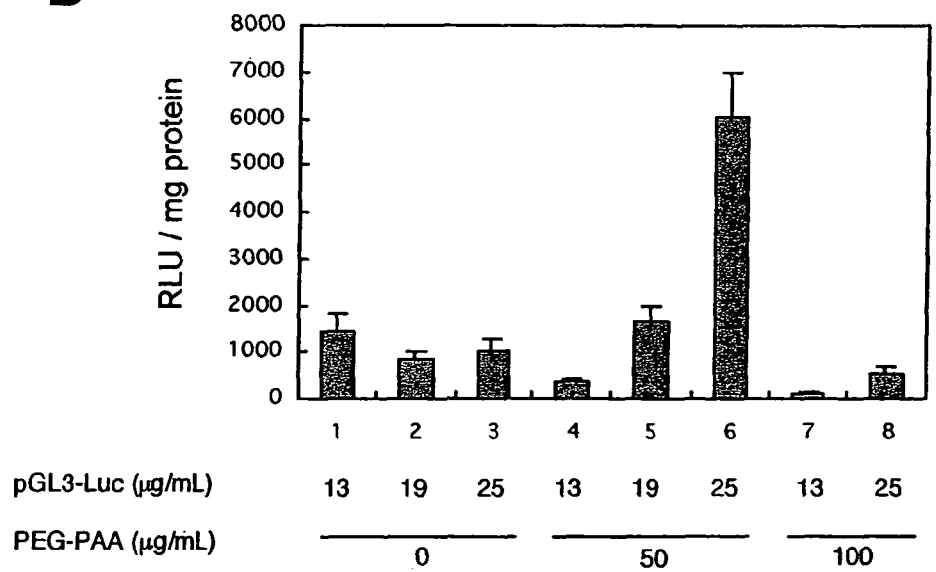

FIGS. 13A and B are graphs showing results obtained by investigating an expression activity of a plasmid DNA-incorporating particle in a cell in Example 10.

BEST MODE FOR CARRYING OUT THE INVENTION

According to the present invention, a block copolymer having a structure represented by Formula (I):

PEG-block-poly(carbo)    (I)

(wherein PEG represents a polyethylene glycol segment, and carbo represents a repetitive unit having a carboxylate ion on a side chain) is characterized by being used in common in a system forming calcium phosphate (hydroxyapatite).

As described above, when referred to as "calcium phosphate" or "hydroxyapatite" in the present specification, it means a mixture of salts which contains mainly calcium phosphate $(Ca_3(PO_4)_2)$ and hydroxyapatite $(Ca_{10}(OH)_2(PO_4)_6)$ and which is formed from a calcium cation $(Ca^{+2})$ and a phosphoric acid anion $(PO_4^{3-})$ in an aqueous solution. It is intended that 50% by weight or more of a salt of a hydroxyapatite type is preferably contained therein.

Poly(carbo) which is one segment in the block copolymer described above represents a polymer segment comprising a repetitive unit having a carboxylate ion at a side chain, and the kind of a starting material providing such repetitive unit does not matter as long as it meets the objects of the present invention. However, capable of being preferably given is a repetitive unit originating in a compound having at least one carboxyl group selected from the group consisting of aspartic acid, glutamic acid, methacrylic acid, acrylic acid and N-acetylhyalobiuronic acid (a repetitive unit of hyaluronic acid). In such Poly(carbo), a fixed carboxyl group can stay in the form of an ester (for example, lower alkyl having up to 6 carbon atoms or benzyl ester) according to a production method of the block copolymer described above. According to the present invention, a residue in the ester of such form may be contained in an amount of up to about 50%, preferably less than 10% and particularly preferably 0% as long as introduction into or adsorption onto calcium phosphate (or hydroxyapatite) is not hindered.

The term "having the structure" represented by Formula (I) intends that a linkage group between PEG and poly(carbo) and an end of PEG or poly(carbo) can have any group or part as long as it meets the objects of the present invention.

A copolymer represented by any one of the following Formulas (II-a), (II-b), (III-a) and (III-b) can be given as the block copolymer particularly preferably used in the present invention:

(II-a)

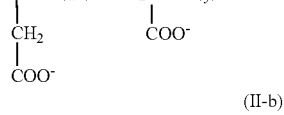

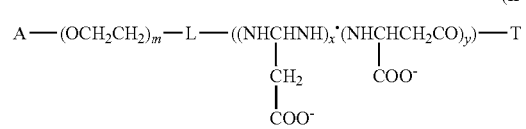

(II-b)

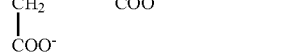

-continued

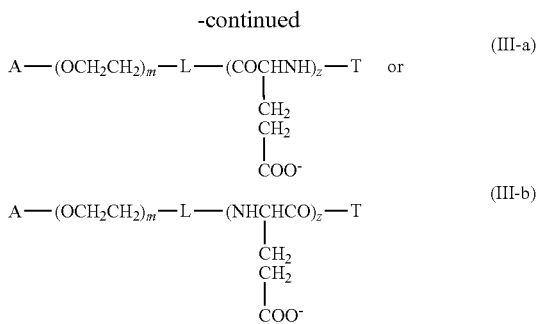

In the respective formulas, the respective codes each have independent meanings;

A represents a hydrogen atom or a substituted or unsubstituted alkyl group having up to 12 carbon atoms;

L represents a single bond, NH, CO or $X(CH_2)_pY$, in which X represents OCO, OCONH, NHCO, NHCOO, NHCONH, CONH or COO; Y represents NH or CO; and p represents an integer of 1 to 6;

T represents a hydrogen atom, a hydroxyl group or —ZR, in which Z represents a single bond, CO, O or NH, and R represents a substituted or unsubstituted hydrocarbon group having up to 12 carbon atoms;

m represents an integer of 4 to 2500; and x+y or z represents an integer of 5 to 300, provided that a carboxylate ion present can form a carboxyester residue in an amount of up to 50%. Also, the mark "·" between an α-aspartic acid unit and a β-aspartic acid unit in Formulas (II-a) and (II-b) described above means that these units are present at random.

The block copolymer in which m is an integer of 12 to 2500 in the formulas described above and in which x+y or z is an integer of 5 to 50 can more preferably be used.

The definitions of the respective groups and the respective parts in the formulas described above have, to be specific, the following meanings. The "alkyl group having up to 12 carbon atoms (hereinafter abbreviated as $C_{12}$, and such describing manner shall be applied as well when representing the other groups having carbon atoms)" is an alkyl group which may be linear or branched and represents, for example, methyl, ethyl, n-propyl, iso-propyl, n-butyl, sec-butyl, n-pentyl, n-hexyl and n- or iso-dodecyl. A substituent for such alkyl groups may be any group as long as it meets the objects of the present invention, and capable of being preferably given are a hydroxyl group, a carboxyl group, a group represented by a formula $R^1R^2CH$— (wherein $R^1$ and $R^2$ represent independently $C_{1-10}$ alkyloxy, aryloxy or aryl-$C_{1-3}$ alkyloxy or represent ethylenedioxy (—O—CH(R')—CH—O—, wherein R' is a hydrogen atom or a $C_{1-6}$ alkyl group) which may be substituted with $C_{1-10}$ alkyl) and a group represented by a formula $R^{1'}R^{2'}NCH_2$— (wherein $R^{1'}$ and $R^{2'}$ represent independently an amino protective group of an organic silyl type, for example, a trialkylsilyl group, or $R^{1'}$ and $R^{2'}$ represent an atomic group which can form a 4- to 7-membered disilaneazacyclo heterocyclic ring together with a nitrogen atom to which they are bonded). For example, the group represented by the formula $R^1R^2CH$— represents so-called acetal or ketal part and can readily be converted to OCH— (aldehyde group) by moderate hydrolysis. On the other hand, the group represented by the formula $R^{1'}R^{2'}NCH_2$— can readily be converted to $H_2N$— in a solution containing, for example, tetraalkylammonium chloride. Accordingly, the block copolymer represented by Formula (II-a), (II-b), (III-a) or (III-b) having such substituent is used to form the organic-inorganic hybrid type particles (for example, polymer micelle) according to the present invention, and then the foregoing substituent which is usually present on the shell or the surface of the above particles is converted to an aldehyde group or an amino group; and polypeptide showing a specific bonding property in, for example, an antibody is advantageously subjected to covalent bonding with the above particles via the functional group thus obtained. Thus, the above particles can be provided with a target directivity. A method for getting a PEG segment having such substituent is known and can be referred to WO96/33233 (or corresponding U.S. Pat. No. 5,925,720) in the case of, for example, the $R^1R^2CH$— group.

The block copolymer described above can be selected from conventionally known ones. It can be produced by forming first a polyethylene glycol segment and then forming a poly (amino acid) segment according to, for example, a method described in Japanese Patent Application Laid-Open No. 107565/1994 or by forming first a polyethylene glycol segment and then forming a poly((meth)acrylic acid) segment according to a method described in WO97/06202. As another method, a conventionally known linkage group may be present, if necessary, between a PEG segment and a poly (carbo) segment. However, the copolymer described above shall not be restricted to those obtained by these production methods, and copolymers which can be obtained by producing in advance independently polymers constituting both segments and then combining them by a suitable method can be used as well in the present invention.

In the block copolymer thus obtained, T in Formulas (II-a), (II-b), (III-a) and (III-b) described above or an end group corresponding thereto is usually a hydrogen atom or a hydroxyl group, and a —ZR group can be introduced into these end groups by a conventionally known method. Such R shall not be restricted, and hydrocarbon groups such as —$CH_3$, —$CH_2CH_3$, —CH=$CH_2$,

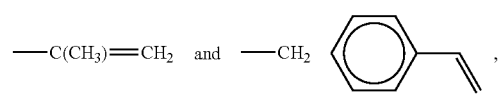

can be given. Such groups can be introduced according to the method described in U.S. Pat. No. 5,925,720 described above.

The biologically active substance which is intended to be or is carried on (or included in) the organic-inorganic hybrid type particles according to the present invention may be any biologically active substance, though shall not theoretically restricted, as long as it is an organic compound which can be included in or adsorbed on a complex or a cross-linked matrix formed by a block copolymer (particularly a carboxylate ion) and a calcium ion or hydroxyapatite. Preferably, however, it may be any biologically active substance selected from the group consisting of poly- or oligonucleotide (used in a concept including DNA or RNA or peptide derivatives thereof) and poly or oligopeptide or derivatives thereof. Such DNA can be a conventionally known cancer-inhibiting gene and others, a gene necessary for maintaining a homemostasis of organisms and an anti-sense of the other specific genes. According to the present invention, these genes can efficiently be introduced into a target cell. Further, in order to use in combination with the organic-inorganic hybrid type particles carried thereon with such genes or independently, polypeptide (including single protein and protein having a sugar chain) which is a proliferative factor known to accelerate a differentiation and inhibit a proliferation in a cell and induce apotosis can be selected as a biologically active substance carried on the above particles. For example, TGF-$\beta_1$, TGF-$\beta_2$, TGF-$\alpha$, connective tissue-activating peptide, a tumor necrotizing factor, an insulin-like proliferative factor, interleukin, a colony stimulating factor and a nerve proliferating factor can be given as these biologically active substances.

The factor effective for healing of wound is included in these proliferative factors, and the organic-inorganic hybrid type particles of then present invention carried thereon with them can be applied to a wound part and used for accelerating healing of wound. Further, if a blood coagulating factor, for example, thrombin is carried as a biologically active substance on the above particles in relation to healing of wound or regardless thereof, it can be used for accelerating hemostatis in combination with a calcium ion or without combining therewith. If the particles carrying (or including) such thrombin are applied to a wound part in a dry state or a concentrated suspension state, it works on fibrinogen present in bleeding blood to form fibrin, which shall bring about so-called hemostatis in situ. Accordingly, a composition containing such particles is useful as a composition for hemostatis.

An antiviral agent, an antibacterial agent, an antihistaminic agent, an antitumor agent and a bone inducing agent may be carried as the other biologically active substance on the above particles according to the present invention as long as they can be carried on the above particles.

According to the present invention, provided is an aqueous dispersion composition for forming the organic-inorganic hybrid type particles carried thereon with the biologically active substance comprising such block copolymer, a calcium ion and a phosphoric acid ion as essential components. The "aqueous dispersion composition" referred to herein or an "aqueous dispersion" referred to later means a solution, a dispersion and a suspension comprising a solvent system which comprises water as a principal solvent and which may contain, if necessary, a small amount of a water-miscible organic solvent (for example, methanol, ethanol and acetone) as long as it does not exert an adverse effect in achieving the objects of the present invention. A buffer which can control the pH to 6.8 to 7.8 is preferably contained in these solutions. A calcium ion and a phosphoric acid ion each contained in these solutions can originate in the respective corresponding water-soluble salts. Typically, the former is derived from calcium chloride, and the latter is derived from disodium hydrogenphosphate.

A content proportion of a calcium ion and a phosphoric acid ion is considerably important in the present invention, and a calcium ion has to be present in an amount which is excessive as compared with an equivalent required for reacting both to form hydroxyapatite ($Ca_{10}(OH)_2(PO_4)_6$). To be specific, a proportion of $Ca^{+2}$ to $PO_4^{3-}$ can be 50 to 200:1 in terms of a mole concentration. When a calcium ion and a phosphoric acid ion are present in such proportion, the block copolymer described above suitably interacts with calcium phosphate (hydroxyapatite) and is bonded, cross-linked or adsorbed.

Further, $Ca^{+2}$ can be present, though shall not be restricted, in an amount of 60 to 300 mM, and $PO_4^{3-}$ can be present, though shall not be restricted, in an amount of 0.4 to 10 mM in the aqueous composition described above. Such proportions are suited for providing the aqueous dispersion comprising the organic-inorganic hybrid type particles carrying or including such biologically active substance, including the aqueous composition described above containing the biologically active substance according to the present invention. To be specific, the block copolymer and the biologically active substance described above suitably interact with calcium phosphate (hydroxyapatite) and are bonded or adsorbed. For example, "the particles carried thereon with the biologically active substance" referred to in the present invention means particles staying in a state in which a part or the whole of the biologically active substance is included in the inside of the particles or in which a part or the whole thereof is present on the surface of the particles.

On the other hand, the block copolymer can be present, though shall not be restricted, in an amount of 10 to 500 μg/ml in the aqueous composition described above. The foregoing concentrations of $Ca^{+2}$ and $PO_4^{3-}$ in the aqueous composition described above and the concentration of the block copolymer described immediately before are usually suited for stably dispersing the organic-inorganic hybrid type particles (containing no biologically active substance) formed in the above aqueous composition or the organic-inorganic hybrid type particles (containing the biologically active substance) in the aqueous dispersion in an aqueous solution. However, the aqueous composition or the aqueous dispersion which meets the objects of the present invention can be provided even if the respective components are used in concentrations exceeding the concentrations described above. Also, such aqueous dispersion can be converted to a dry form by a conventional method, for example, a dry freezing method. The composition of such dry form can be constituted again to a stable aqueous dispersion by adding an aqueous medium. Further, it can be turned, if necessary, into a formulation of another form using another binders as it stays in the dry form.

The organic-inorganic hybrid type particles described above (containing no biologically active substance) can be used for forming fine or microscopic hydroxyapatite of a submicron order having a uniform particle diameter. Such particles can be obtained, if necessary, by removing excess $Ca^{+2}$ by dialysis and then freeze-drying.

The aqueous dispersion according to the present invention which has already been partially referred to in the above can be prepared by allowing the biologically active substance to coexist in the aqueous composition described above. To be more specific, it can be prepared by, though shall not be restricted, (A) preparing a first aqueous solution containing a biologically active substance, a calcium ion and, if necessary, a buffer, (B) preparing independently a second aqueous solution containing the block copolymer having the structure represented by Formula (I):

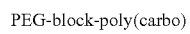

PEG-block-poly(carbo)　　　　(I)

(wherein PEG represents a polyethylene glycol segment, and carbo represents a repetitive unit having a carboxylate ion at a side chain), a phosphoric acid ion and, if necessary, a buffer and (C) mixing the first aqueous solution described above with the second aqueous solution on a condition enough for forming hydroxyapatite. A salt such as sodium chloride can be contained in the second aqueous solution, and when the buffer is used, it is preferably selected so that a pH of the final dispersion can be controlled to 6.8 to 7.8.

Though shall not be restricted to such production method, the particles contained in the aqueous suspension according to the present invention are particles carried thereon with the biologically active substance which are formed from the block copolymer described above, a calcium ion, a phosphoric acid ion and the biologically active substance and have an average particle diameter of 50 to 600 nm. According to the foregoing production method of the present invention, an aqueous dispersion containing very uniform particles in which an average particle diameter has any size of 50 to 600 nm and in which a polydispersity is 0.1 or less can be provided by selecting a concentration of the block copolymer. It is a matter of course that particles having a particle diameter of a several μm order exceeding 600 nm can be formed, if necessary, by extending preparing time. These aqueous dispersions can be stored for several days to one month on an ambient condition (for example, room temperature) without substantially causing precipitation or phase separation, and therefore they can be used as a composition for injection as they are or, if necessary, by removing excess ionic low molecular compounds by dialysis or ultrafiltration.

The biologically active substance which can be carried on such particles is, though described above, generally a compound which can show any useful activity in organisms of animals (particularly human beings) and can be polynucleotide (including DNA, mRNA and the like) coding exotic active peptide, polynucleotide coding a function which promotes or controls revelation of a specific gene, polynucleotide such as anti-sense DNA and ribozime and polypeptide (including protein and, as long as the objects are met, oligopeptide). These peptides preferably contain a polyvalent carboxyl group.

The organic-inorganic hybrid type particles according to the present invention comprise typically, though shall not be restricted, 30 to 70% by weight of the block copolymer,
25 to 65% by weight of hydroxyapatite and
0.1 (preferably 1) to 15% by weight of the biologically active substance each based on the whole weight of the above particles.

The production method for the aqueous dispersion according to the present invention can be provided by carrying out the specific embodiment in the presence of a cultured cell, for example, as a method for introducing polynucleotide into an animal cell, characterized by:

(A) adding an aqueous dispersion comprising organic-inorganic hybrid type particles carried thereon with a biologically active substance to a cultured substance of an animal cell, wherein the above particles are formed from a block copolymer having a structure represented by Formula (I):

PEG-block-poly(carbo)     (I)

(wherein PEG represents a polyethylene glycol segment, and carbo represents a repetitive unit having a carboxylate ion on a side chain), a calcium ion ($Ca^{+2}$), a phosphoric acid ion ($PO_4^{3-}$) and the above biologically active substance; the above particles have an average particle diameter of 50 to 600 nm; and the above biologically active substance is selected from the group consisting of poly- or oligonucleotide and poly- or oligopeptide and (B) incubating the cultured substance prepared in (A).

According to such method, the particles can slowly be dissolved under a physiologic condition by reducing a concentration of the block copolymer in forming the particles described above, and on the other hand, the particles can stably be maintained under the physiologic condition by elevating a concentration of the block copolymer, which makes it possible as well to control a discharge time of the biologically active substance in a target part. For example, DNA as the biologically active substance is introduced into a cell in the form of the organic-inorganic hybrid type particles described above, and it can be delivered to the nucleus of the cell while avoiding decomposition caused by nuclease in the cell. Such a high efficiency of introducing DNA into a cell can be achieved as well when the composition of the present invention is injected into the suited part of an organism, that is, in a system in vivo.

As shown above, according to the present invention, the aqueous dispersion comprising the organic-inorganic hybrid type particles which can be a carrier for a biologically active substance or the composition of a dry form can be provided, or the aqueous composition used for providing the same and the preparing method for them can be provided.

The present invention shall more specifically be explained below while giving the examples of the specific embodiments of the present invention in order to simplify the explanations, but the present invention shall not be intended to be restricted to them.

Example 1

Experiment for Confirming Action and Effect of Block Copolymer

This experiment shows that a specific block copolymer is effective for an inhibition in the formation of precipitates of calcium phosphate (hereinafter abbreviated as CaP) or a controlled formation in particles having a fixed particle diameter or less.

<Experimental Method>

(1) The following aqueous solution was prepared:

| | |
|---|---|
| Solution A: | DNA (16 mer: 70 μg/mL) |
| | 1/10 TE buffer (pH 7.6) |
| | $Ca^{+2}$ 250 mM (using $CaCl_2$) |
| Solution B: | $PO_4^{3-}$ 1.5 mM (using $Na_2HPO_4$) |
| | Hepes buffer 50 mM (pH 7.05) |
| | NaCl 140 mM |
| | poly(aspartic acid) homopolymer |
| | (hereinafter abbreviated as PAA) or PEG- |
| | block-poly (aspartic acid) (hereinafter |
| | abbreviated as PEG-PAA; PEG molecular |
| | weight: 12000, PAA polymerization degree: 24) |

In the above, PAA is poly(α,β)-DL-aspartic acid, and a compound having a molecular weight of 2000 to 10000 (polymerization degree: 15 to 77) (obtained from SIGMA) is used. PEG-PAA is represented by the following formula:

$$CH_3O(CH_2CH_2O)_n-(COCH(CH_2COO^-)NH)_x-(COCH_2CH(COO^-)NH)_yH$$

and a compound in which a PEG segment had a molecular weight of about 12000 and in which a PAA segment had a polymerization degree (x+y) of 24 was produced and used.

(2) The solution A was mixed with the solution B at 37° C. to trace a change in a turbidity from a transmission factor of light having a wavelength of 350 nm.

<Result>

Figure 1:
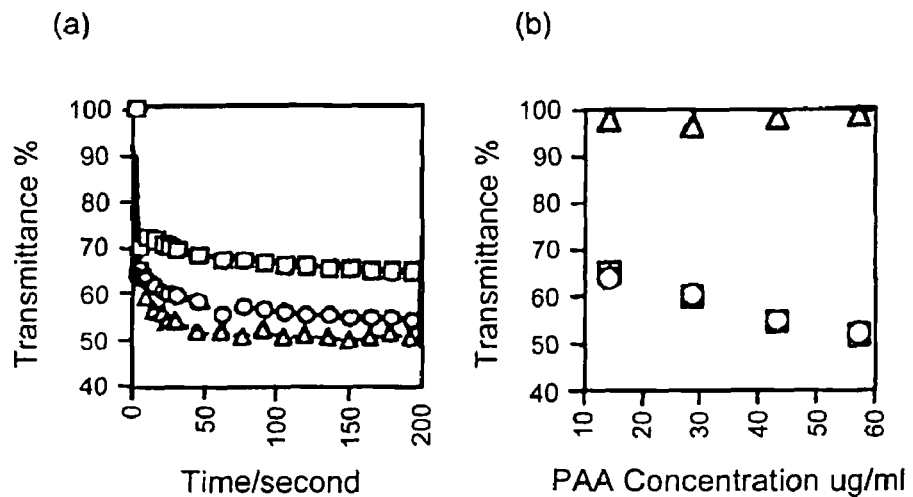
FIG. 1 is a graph showing an influence of PAA and PEG-PAA exerted to a growth in crystal of CaP, wherein (a) is a graph showing a change in a transmittance with the passage of time in the presence of PAA (PAA concentration: (□) 14 μg/mL, (○) 43 μg/mL and (Δ) 57 μg/mL), and (b) is a transmittance after 3 minutes since mixing the solutions (((□) PAA, (○) PEG/PAA (blended) and (Δ) PEG-PAA).

The result is shown in FIG. 1. When a homopolymer of PAA was added, the transmission factor was suddenly reduced immediately after mixing the solutions. The degree thereof was dependent on a PAA concentration, and the higher the polymer concentration was, the more largely the transmission factor was changed (FIG. 1a). In this case, if PEG coexisted, the transmission factor was not changed, and it was suggested that PEG did not interact with precipitate (FIG. 1b). On the other hand, it was shown that the transmission factor was scarcely changed under the presence of the block copolymer and that precipitate was inhibited from being formed. It is apparent from these results that the copolymer structure is necessary for inhibiting precipitation of DNA-including CaP.

Example 2

Particle Diameter of Composite Particles of DNA and Calcium Phosphate (No. 1)

The solution A was mixed with the solution B in the same manner as in Example 1 to prepare an aqueous dispersion containing composite particles. The dispersion was left standing still at 37° C. for a night after mixing, and then the particle diameter was evaluated by dynamic light scattering (DLS) measurement of the dispersion.

DSL-7000 manufactured by Ohtsuka Electron Co., Ltd. was used as the measuring apparatus. A light of argon laser having a wavelength of 488 nm was used as an incident light to carry out the measurement at 25° C. A scattered light at an angle 90° to the incident light was detected to analyze a time dependency in an intensity change thereof by a cumulant method, whereby a diffusion coefficient of the particles was determined. The diffusion coefficient thus obtained was converted to the particle diameter according to the following equation of Stokes-Einstein:

$$R = kT/(6\pi\eta D)$$

wherein R=particle diameter, k=Boltzmann's constant, $\eta$=viscosity coefficient, D=diffusion coefficient <Result>

Figure 2:
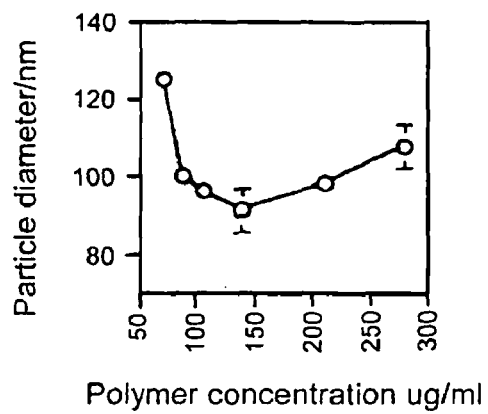
FIG. 2 is a graph showing a result of measuring a particle diameter of CaP particles by dynamic light scattering.

The result of measuring the CaP particles by dynamic light scattering is shown in FIG. 2. It was confirmed by DLS measurement that the particles were formed. The particle diameter thereof was 125 nm at a PEG-PAA concentration of 70 µg/ml and decreased as the copolymer concentration was increased, and it was about 90 nm at 140 µg/ml. Then, the particle diameter was elevated again as the copolymer concentration was increased.

Figure 3:
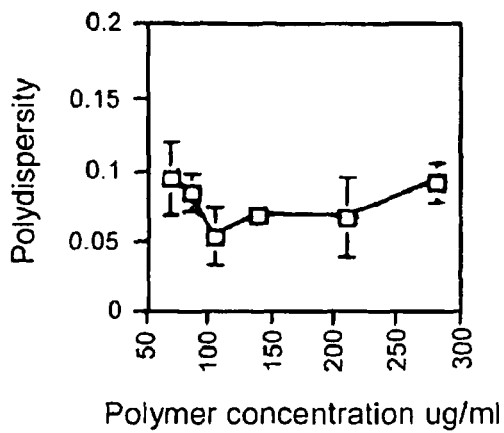
FIG. 3 is a graph showing a change in a polydispersity of CaP particles to a PEG-PAA concentration.

Further, the polydispersity which was an index of a size in a particle diameter distribution of the particles was determined similarly by the cumulant method to find that it was 0.1 or less. This value is a deviation of a standardized diffusion coefficient, and when it is 0.1 or less, it is usually regarded as monodispersibility in a colloidal particle. Refer to FIG. 3.

Example 3

Particle Diameter of Composite Particles of Calcium Phosphate Containing No DNA

Figure 4:
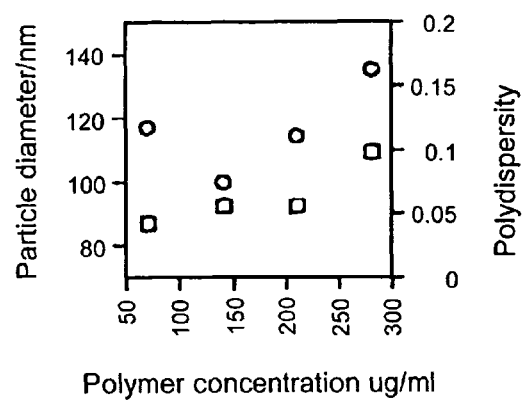
FIG. 4 is a graph showing the same measuring result as in FIGS. 2 and 3 regarding particles prepared without adding DNA in preparing the particles.

The same procedure as in Example 2 was repeated, except that a solution obtained by removing DNA from the solution A prepared in Example 1 was used in producing composite particles. The result thereof is shown in FIG. 4. The particle diameter and the polydispersity are almost the same as in Example 2.

Example 4

Determination of Amount of DNA Introduced (or Included) into Particles (No. 1)

CaP particles were prepared on the same condition as in Example 2. The aqueous dispersion thus prepared was subjected to high performance liquid chromatography (HPLC) on the following conditions to quantitatively determine DNA.

HPLC condition: column Superose 6HR (room temperature)
Eluent 1 $CaCl_2$ 125 mM, 140 mM NaCl, 50 mM HEPES, pH 7.4
Eluent 2 $CaCl_2$ 200 mg/L (calcium ion 1.8 mM), $NaH_2PO_4 \cdot H_2O$ 125 mg/L (phosphoric acid ion 0.9 mM) NaCl 6400 mg/L, HEPES 5958 mg/L, pH 7.4
Detection UV 260 nm <Result>

Figure 5:
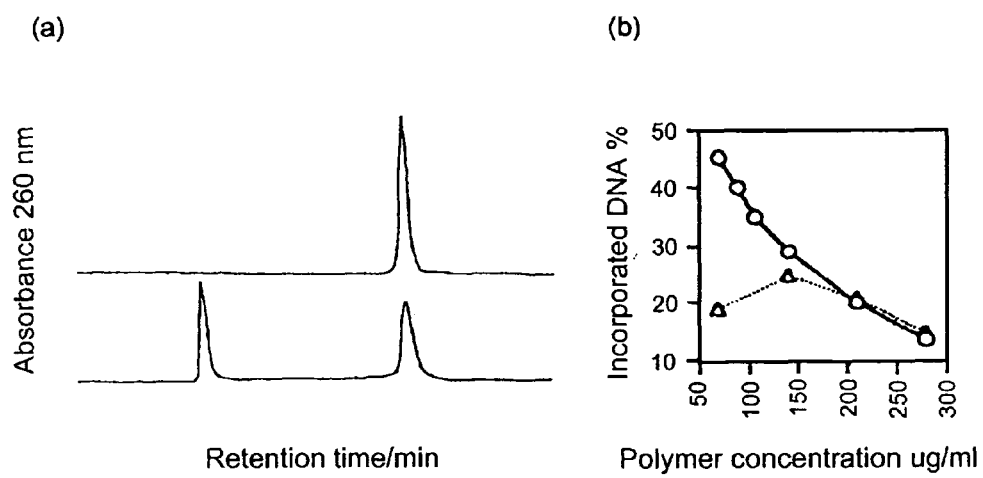
FIG. 5 is an elution pattern showing a result of determining DNA included in CaP particles by HPLC; (a) upper line: only DNA and (b) a graph showing a change in an amount of included DNA to a PEG-PAA concentration ((○): eluate 1 and (Δ): eluate 2).

The measuring result of HPLC is shown in FIG. 5. In the case of DNA alone, a peak originating in DNA was observed in the vicinity of an elution time of 30 minutes. On the other hand, in the case of the CaP solution, a peak originating in the particles was confirmed together with a peak originating in DNA in the vicinity of an elution time of 12 minutes. A proportion of DNA included in the particles was calculated from comparison of a ratio of both.

Under the conditions of the eluent 1, DNA was decreased from an including amount of 45% in a PEG-PAA concentration of 70 µg/mL as the concentration was increased.

In the case where the eluent 2 which was close to a physiologic condition was used, it was suggested that the particles were slowly dissolved at a low polymer concentration. On the other hand, it was suggested that the particles were stable at a high polymer concentration even on a physiologic condition.

A composition weight ratio of the CaP particles formed can be converted in the following manner.

Assuming that calcium is largely excessive in a solution containing 125 mM of calcium and 0.75 mM of phosphoric acid and that all of phosphoric acid molecules are turned into CaP, the composition of CaP is $Ca_2(OH)(PO_4)_3$, and therefore a CaP weight concentration is 126 µg/ml (Table 1). Further, assuming that all of PRG-PAA added are adsorbed on CaP, the composition ratio shown in Table 2 is obtained.

TABLE 1

Weight concentration in components of CaP particle solution

| Sample No. | PRG-PAA (µg/ml) | CaP (µg/ml) | DNA (µg/ml) | Total (µg/ml) |
|---|---|---|---|---|
| 1 | 70 | 126 | 16 | 212 |
| 2 | 140 | 126 | 11 | 277 |
| 3 | 210 | 126 | 7 | 343 |
| 4 | 280 | 126 | 5.3 | 411 |

TABLE 2

Component composition ratio of CaP particles

| Evaluation No. | PRG-PAA/ weight % | CaP/ weight % | DNA/ weight % |
|---|---|---|---|
| 1 | 33 | 60 | 7.4 |
| 2 | 51 | 46 | 3.8 |
| 3 | 61 | 37 | 2 |
| 4 | 68 | 31 | 1.3 |

The eluents 1 and 2 described in the experiments described above were used for the following purposes respectively.

Eluent 1: a calcium concentration of 125 mM in the eluent 1 is the same as that of the CaP particle solution. The calcium concentration is largely excessive to that of phosphoric acid on this condition, and it is considered that the CaP particles are not dissolved. In this case, this eluent was used to determine a DNA-including amount in the CaP particles prepared.

Eluent 2: a factor exerting an effect on the stability of the particles on a physiological condition is the concentrations of calcium and phosphoric acid contained in the solution. In this case, a solution containing calcium and phosphoric acid each having a concentration close to the physiological condition was used as the eluent to evaluate the stability of the particles on the physiological condition.

Example 5

Movement of DNA Included in Particles in Cell

CaP particles were prepared in the same manner as in Example 1. Provided that DNA of 20 mer subjected to fluorescent labeling with Rhodamine was used. The aqueous dispersion was left standing still at 25° C. for a night and then worked on a cell.

Experiment of Action on Cell

A cell strain HuH-7 (originating in human liver cancer, obtained from Riken Gene Bank) was cultivated at 37° C. under 5% $CO_2$ atmosphere using a culture medium prepared by adding 10% fetal calf serum to DMEM (Dulbecco's modified eagle medium; obtained from GIBCO BRL).

Figure 6:
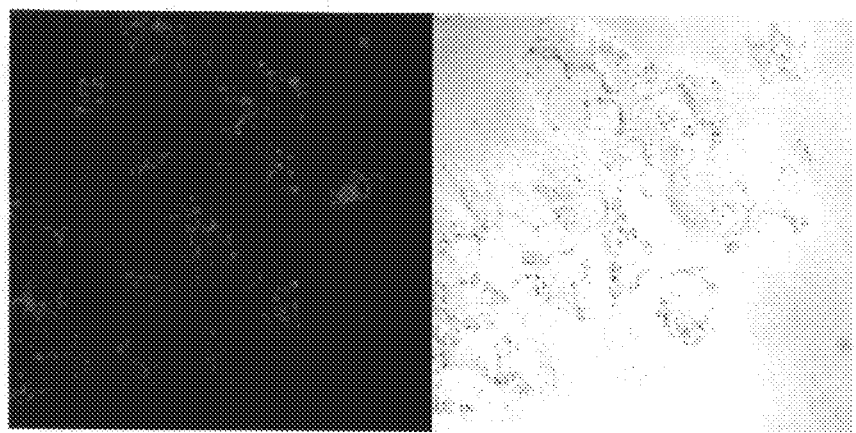
In FIG. 6, A) is a microscopic image in place of a drawing showing the state of a cell after working only DNA on the cell. In this case, granular fluorescence indicating introduction by endocytosis is observed.
Figure 6:
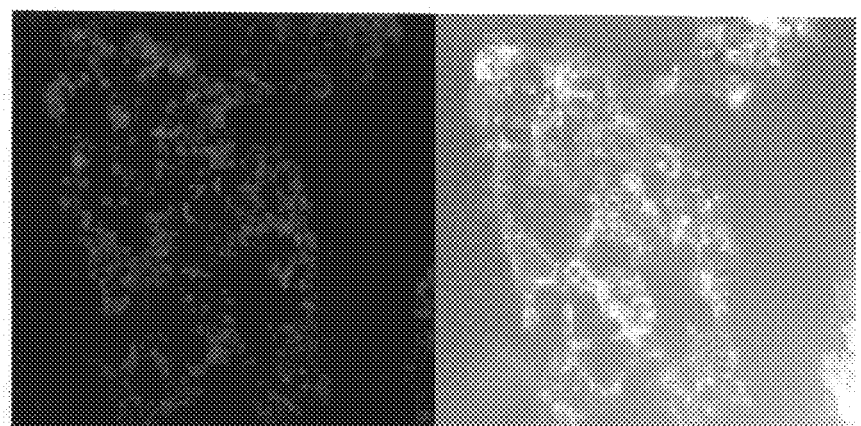

The aqueous dispersion was added to the cultured substance described above in a proportion of 1 to 9 of the CaP particle-containing aqueous dispersion to the culture medium in terms of a volume ratio to cultivate the strain for 3 hours, and then the culture medium was removed, followed by washing the strain three times with PBS. This was observed under a confocal laser microscope LSM510 (manufactured by Carl Zeiss Co., Ltd.). Photographs in place of drawings showing the state of the treated cells are attached as FIG. 6 to 8.

CaP/DNA was adsorbed on the surface of the cell on a condition on which a precipitate was formed (*precipitate was observed in PEG-PAA 70 μg/ml because of a difference in a DNA chain length). On the other hand, it was suggested from a granular fluorescent image that the CaP particles were introduced into the cell by endocytosis.

Further, it was suggested that when adding (35 μg/mL, DNA 35 μg/mL) poly(methacrylic acid) (molecular weight 9500; obtained from Aldrich Chemical Company Inc.) in forming the particles, DNA is localized in the nucleus of the cell. DNA is distributed in the cytoplasma only with Rhodamine, and therefore it is considered that DNA is not broken to excess in this case.

Example 6

Particle Diameter of Composite Particles of DNA and Calcium Phosphate (No. 2)

It was shown in Example 2 that a particle diameter of the composite particles could be controlled by changing a concentration of the copolymer, and it shall be shown in the present example that the above particle diameter can further be controlled by changing a concentration of phosphoric acid together with a concentration of the copolymer.

<Experiment>

(1) The following solution was prepared:

| | |
|---|---|
| Solution A: | DNA (16 mer: 70 μg/mL) |
| | 1/10 TE buffer (pH 7.6) |
| | $Ca^{+2}$ 250 mM (using $CaCl_2$) |
| Solution B: | $PO_4^{3-}$ 1.5 mM, 3.0 mM or 6.0 mM (using $Na_2HPO_4$) |
| | Hepes buffer 50 mM (pH 7.05) |
| | NaCl 140 mM |
| | PEG-PAA (PEG molecular weight: 12000, PAA polymerization degree: 24) |
| | 140 to 1400 μg/mL |

(2) The solution A was mixed with the solution B each in the same amount, and the dispersion was left standing still at 37° C. for a night. Then, a particle diameter and a polydispersity of the particles were determined by dynamic light scattering measurement.

<Result>

As shown in FIG. 9(*a*), a particle diameter of the particles formed was changed by the concentrations of PEG-PAA and phosphoric acid, and as shown in FIG. 9(*b*), the uniform particles having a polydispersity of 0.1 or less and a particle diameter of 100 to 300 nm were obtained in any concentration. The marks □, ◇ and ○ in FIG. 9(*a*) and (*b*) each correspond to the phosphoric acid concentrations of 0.75 mM, 1.5 mM and 3.0 mM.

Example 7

Determination of Amount of DNA Introduced (or Included) into Particles (No. 2)

Particles prepared according to Example 6 were quantitatively determined for an including amount of DNA in the same manner as described in Example 4.

<Result>

The measurement result of HPLC is shown in FIG. 10. It is observed from the drawing that an including amount of DNA tends to go up as a concentration of phosphoric acid is increased. An inclusion rate of DNA reached 90% in 3.0 mM of phosphoric acid and 540 μg/mL of PEG-PAA. Comparing the results of the eluent 1 with those of the eluent 2, the inclusion rate was observed to be decreased in the eluent 2 in which a calcium concentration and a phosphoric acid concentration were close to those of a human being. In the drawing, a void shows a result obtained by using the eluent 1, and a solid mark shows a result obtained by using the eluent 2. Numerals in the drawing means the phosphoric acid concentrations.

Example 8

Introduction of DNA-Including Particles Into Cell

Experiment

1. Particle Preparing Condition (1) The following solution was prepared:

| | |
|---|---|
| Solution A: | DNA (16 mer: 70 μg/mL) |
| | (5' end was labelled with FITC) |
| | 1/10 TE buffer (pH 7.6) |
| | $Ca^{+2}$ 250 mM |

-continued

| | |
|---|---|
| Solution B: | $PO_4^{3-}$ 6.0 mM |
| | Hepes buffer 50 mM (pH 7.05) |
| | NaCl 140 mM |
| | PEG-PAA (PEG molecular weight: 12000, PAA polymerization degree: 24) |
| | 1080 µg/mL |

(2) The solutions A and B were mixed in the same amount and left standing still at 37° C. for 24 hours.

2. Evaluation for Introducing Cell

An HeLa cell (human cervix cancer cell) was put on a 24-well plate in a cell density of $2×10^4$/well and cultivated in a DMEM culture medium (containing 10% FCS) for 24 hours. Then, 50 µL of the particles or a DNA sample was added to 450 µL of the culture medium (DMEM, 10% FCS). After prescribed time passed, the cell was peeled off by trypsinization and dispersed in 1 to 2 mL of PBS (cooled with ice until measurement). The cell of about $2×10^3$ was analyzed by flow cytometry.

A gate was applied so that the untreated cell having the strongest fluorescent intensity was contained in a proportion of 1%. A fluorescent intensity of the untreated cell had an average value of 0.5.

<Result>

The results are shown in FIG. 11(a), (b) and (c). It can be found from the drawing that DNA alone is scarcely observed to be introduced on the experimental condition described above. On the other hand, it has been apparent that introduction of DNA into the cell is increased to a large extent by allowing DNA to be incorporated in the particles and that nucleic acid is introduced into almost 100% of the cells in 4 hours. It can be found as well from a result obtained by plotting an average fluorescent intensity of the cell that introduction of DNA into the cell is promoted to a large extent as compared with DNA alone by making use of the particles.

FIG. 11(a) is a typical histogram (after 24 hours) of the untreated cell and the cell treated with the CaP particles; (b) shows a change in an amount of introducing DNA into a cell versus time (shown by % of the cell present in a gate area); and (c) shows a change in an amount of introducing DNA into a cell versus time (shown by the average fluorescent intensity).

Example 9

Toxicity Evaluation Test of Particles

Experimental Method

1. Particle Preparing Conditions (1) The following solution was prepared:

| | |
|---|---|
| Solution A: | DNA (16 mer: 70 µg/mL) |
| | 1/10 TE buffer (pH 7.6) |
| | $Ca^{+2}$ 250 mM |
| Solution B: | $PO_4^{3-}$ 1.5 mM |
| | Hepes buffer 50 mM (pH 7.05) |
| | NaCl 140 mM |
| | PEG-PAA (PEG molecular weight: 12000, PAA polymerization degree: 24) |
| | 140 to 560 µg/mL |

(2) The solutions A and B were mixed in the same amount and left standing still at 37° C. for 24 hours.

2. Toxicity Test

An HeLa cell (human cervix cancer cell) was put on a 96-well plate in a cell density of $5×10^3$/well and cultivated in a DMEM culture medium (containing 10% FCS) for 2 days. Then, 10 µL of a particle sample was added to 90 µL of the culture medium (DMEM, 10% FCS). After cultivated for 24 hours, the viable cell number was counted by MTT (3-(4,5-dimethyl-2-thiazolyl)-2,5-diphenyl-2H-tetrazolium bromide) assay.

The MTT assay was carried out in the following manner.

An MTT (5 mg/mL (PBS)) solution was added in an amount of 10 µL per well of the 96-well plate and left standing still at 37° C. for 2 hours. Then, 20% SDS (DMF:water=1:1) was added in an amount of 100 µL per well and left standing still at 37° C. for 24 hours. The absorbance at 560 nm was measured by a plate leader.

<Result>

The result is shown in FIG. 12. FIG. 12 shows percentage of a viable cell number to an untreated cell by a bar graph. According to this graph, it is apparent that the viable cell number is not decreased as compared with the untreated cell within an experimental error range and that the particles do not show a marked toxicity under the existing experimental conditions.

Example 10

Transfection Experiment

Plasmid DNA (coded with a luciferase gene) was used as included nucleic acid in the following experiment to investigate an ability of the particles for introducing a gene into a cell.

<Experimental Method>

1. Particle Preparation (1) The following solution was prepared:

| | |
|---|---|
| Solution A: | Plasmid DNA (pGL3-Luc, 5 kbp) |
| | (26 to 50 µg/mL) |
| | 1/10 TE buffer (pH 7.6) |
| | $Ca^{+2}$ 250 mM |
| Solution B: | $PO_4^{3-}$ 1.5 mM |
| | Hepes buffer 50 mM (pH 7.05) |
| | NaCl 140 mM |
| | PEG-PAA (PEG molecular weight: 12000, PAA polymerization degree: 24) |
| | 100 to 200 µg/mL |

(2) The solutions A and B were mixed in the same amount and left standing still at 25° C. for 24 hours.

2. Transfection Experiment 293T cell (human kidney) was put on a 6-well dish (coated with gelatin) so that 60% confluent was achieved and cultivated in a DMEM culture medium (containing 10% FCS) for 24 hours. After removing the culture medium, the cell was washed with PBS, and a new culture medium was added thereto. Then, the sample was added in an amount of 100 µL per mL of the culture medium and cultivated for 6 hours. After exchanging the culture medium, the cell was further cultivated for 24 hours. The luciferase gene-revealing amount was quantitatively determined by means of a commercial assay kit.

<Result>

The results are shown in FIGS. 13A and B. FIG. 13A shows a result obtained by examining an influence of a PEG-PAA temperature and the presence of a blood serum in cultivating for 6 hours to the revelation of a gene. The activity which was higher by 4 to 6 times as compared with that in 0 µg/mL was observed in 50 µg/mL of PEG-PAA. Further, it is apparent that the activity revealed is decreased as the PEG-PAA concentration is increased to 75 and 100 µg/mL.

The expression amount is reduced on the condition of 50 and 75 µg/mL in the presence of a blood serum as compared with in the absence thereof, but the activity which is higher than or equivalent to that in 0 µg/mL is obtained.

FIG. 13B shows a result obtained by examining an influence of the plasmid DNA concentration to the revelation of a gene.

In a PEG-PAA concentration of 0 µg/mL, a notable difference in revelation caused by the plasmid DNA concentration was not observed. On the other hand, in 50 µg/mL, the revelation went up as the plasmid DNA concentration was raised.

INDUSTRIAL APPLICABILITY

The organic-inorganic hybrid particle according to the present invention is useful for introducing a biologically active substance (for example, DNA) into, for example, a cell and expressing it. Accordingly, the present invention is applicable in the medical industry and the pharmaceutical industry.

The invention claimed is:

1. A composition comprising organic-inorganic hybrid particles having a biologically active substance carried thereon, wherein the particles are formed from a block copolymer having a structure represented by any one of the following Formulas (II-a), (II-b), (III-a) and (III-b):

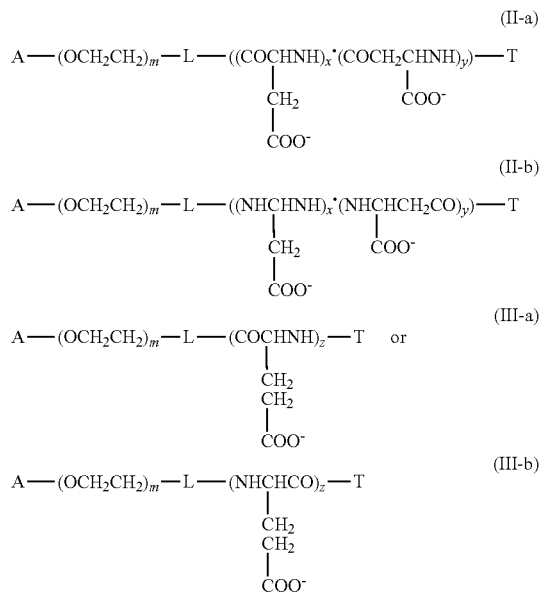

where in the respective formulas, A, L, T, m, x, y and z each have the following independent meanings;

A represents a hydrogen atom or a substituted or unsubstituted alkyl group having up to 12 carbon atoms;

L represents a single bond, NH, CO or $X(CH_2)_p Y$, in which X represents OCO, OCONH, NHCO, NHCOO, NHCONH, CONH or COO; Y represents NH or CO; and p represents an integer 1 to 6;

T represents a hydrogen atom, a hydroxyl group or —ZR, in which Z represents a single bond, CO, O or NH, and R represents a substituted or unsubstituted hydrocarbon group having up to 12 carbon atoms;

m represents an integer of 4 to 2500; and x+y or z represents an integer of 5 to 300, a calcium ion ($Ca^{+2}$), a phosphoric acid ion ($PO_4^{3-}$) and the biologically active substance, and the particles have an average particle diameter of 50 to 600 nm in an aqueous dispersion, and are substantially spherical, wherein the calcium ion is present in the hybrid particles in an amount which is excessive to the phosphoric acid ion as compared with an equivalent required for forming hydroxyapatite, and wherein the organic-inorganic hybrid particles comprise 30 to 70% by weight of the block copolymer, 25 to 65% by weight of hydroxyapatite and 0.1 to 15% by weight of the biologically active substance each based on the whole weight of the particles.

2. The composition as described in claim 1, wherein m is 12 or more, and x+y or z is 50 or less.

3. The composition as described in claim 1, wherein the organic-inorganic hybrid particles have any diameter of an average particle diameter of 50 to 600 nm and a polydispersity of 0.1 or less in the aqueous dispersion.

4. The composition as described in claim 1, wherein the biologically active substance is selected from the group consisting of poly- or oligonucleotide and poly- or oligopeptide.

5. The composition as described in claim 1, wherein the composition comprising the organic-inorganic hybrid particles has the form of an aqueous dispersion.

6. The composition as described in claim 1, wherein the composition comprising the organic-inorganic hybrid particles has a freeze-dried form.

7. A method for preparing the composition as described in claim 1, comprising:

(A) a step of preparing a first aqueous solution containing a biologically active substance, and a calcium ion, (B) a step of preparing independently a second aqueous solution containing a block copolymer having a structure represented by any one of the following Formulas (II-a), (II-b), (III-a) and (III-b):

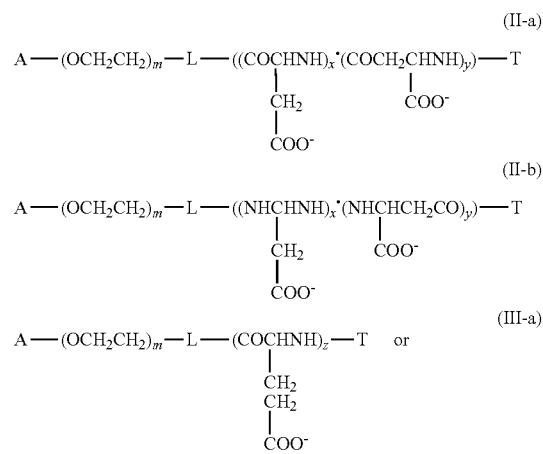

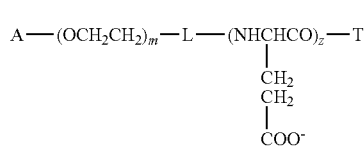

(III-b)

where in the respective formulas, A, L, T, m, x, y, and z each have the independent meanings recited in claim 6; and a phosphoric acid ion and (C) a step of mixing the first aqueous solution with the second aqueous solution to form hydroxyapatite, wherein the calcium ion is present in the hybrid particles in an amount which is excessive to the phosphoric acid ion as compared with an equivalent required for forming hydroxyapatite, and wherein the organic-inorganic hybrid particles comprise 30 to 70% by weight of the block copolymer, 25 to 65% by weight of hydroxyapatite and 0.1 to 15% by weight of the biologically active substance each based on the whole weight of the particles.

8. The method as described in claim 7, wherein a proportion of $Ca^{+2}$ to $PO_4^{3-}$ is 50 to 200:1 in terms of mole concentration.

9. The method as described in claim 7, wherein the biologically active substance is selected from the group consisting of poly- or oligonucleotide and poly- or oligopeptide.

10. The composition as described in claim 1, wherein a proportion of $Ca^{+2}$ to $PO_4^{3-}$ is 50 to 200:1 in terms of mole concentration.

11. A method for producing a dispersion comprising organic-inorganic hybrid type particles having an average particle diameter of 50 to 600 nm, comprising a step of carrying out reaction using a calcium ion and a phosphoric acid ion in an aqueous solution in which a block copolymer represented by any one of the following Formulas (II-a), (II-b), (III-a) and (III-b) is present, wherein an excess calcium ion exceeding an equivalent required for forming hydroxyapatite is used:

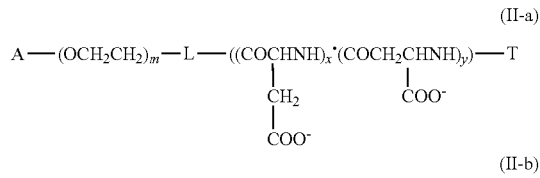

(II-a)

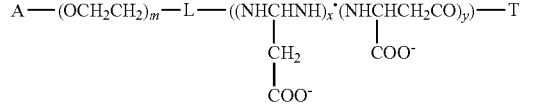

(II-b)

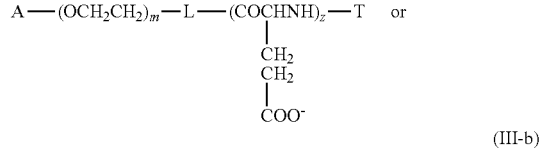

(III-a)

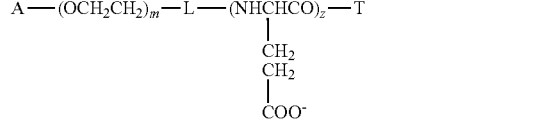

(III-b)

in the respective formulas, the respective codes each have independent meanings;

A represents a hydrogen atom or a substituted or unsubstituted alkyl group having up to 12 carbon atoms;

L represents a single bond, NH, CO or $X(CH_2)_pY$, in which X represents OCO, OCONH, NHCO, NHCOO, NHCONH, CONH or COO; Y represents NH or CO; and p represents an integer of 1 to 6; T represents a hydrogen atom, a hydroxyl group or —ZR, in which Z represents a single bond, CO, O or NH, and R represents a substituted or unsubstituted hydrocarbon group having up to 12 carbon atoms;

m represents an integer of 4 to 2500; and x+y or z represents an integer of 5 to 300, provided that a carboxylate ion present can form a carboxyester residue in an amount of up to 50%, wherein the particles are substantially spherical and comprise 30 to 70% by weight of the block copolymer and 25 to 65% by weight of hydroxyapatite.

* * * * *